United States Patent [19]

Lindstrom

[11] Patent Number: 5,002,569
[45] Date of Patent: Mar. 26, 1991

[54] INTRAOCULAR LENS

[76] Inventor: Richard L. Lindstrom, 1065 W. Ferndale Rd., Wayzata, Minn. 55391

[21] Appl. No.: 529,883

[22] Filed: May 29, 1990

Related U.S. Application Data

[63] Continuation of Ser. No. 43,319, Apr. 28, 1987, abandoned, which is a continuation of Ser. No. 837,135, Mar. 7, 1986, abandoned.

[51] Int. Cl.⁵ ............................... A61F 2/16
[52] U.S. Cl. ..................................... 623/6
[58] Field of Search ............................. 623/6

[56] References Cited

U.S. PATENT DOCUMENTS 4,485,499 12/1984 Cstleman .................. 623/6
4,547,914 10/1985 Cstleman .................. 623/6

OTHER PUBLICATIONS

New Nova Aid Kratz Elliptical Posterior Chamber Lens Model 822, Advertisement (3 pages), Coopervision, Coopervision IOL, 3190 160th Ave. S.E., Bellevue, WA 98008, 623≧626 1983.

Primary Examiner—Ronald Frinks
Attorney, Agent, or Firm—Hugh D. Jaeger

[57] ABSTRACT

An intraocular lens denoted as a YAG dimpled lens or dimpled YAG lens, which includes a barrier rim and a YAG spacer area in a posterior surface of the lens. The barrier rim is 2–4 mm in longitudinal length and the YAG spacer is 3–4 mm in longitudinal length across the surface diameter of an optic of the intraocular lens. The lens optic can be either plano-convex or bi-convex. A cutout for the dimpled YAG spacer is provided which is either a convave or a substantially rectangular geometrical configuration in the posterior surface of the lens. The YAG spacer can also include a trough or a groove geometrical configuration, such as in the configurations of a Maltese cross, a circular trough or groove, or a circular trough or groove with a Maltese cross therein. The barrier rim is 33% to 80% of the total surface are of the posterior surface of the lens.

2 Claims, 9 Drawing Sheets

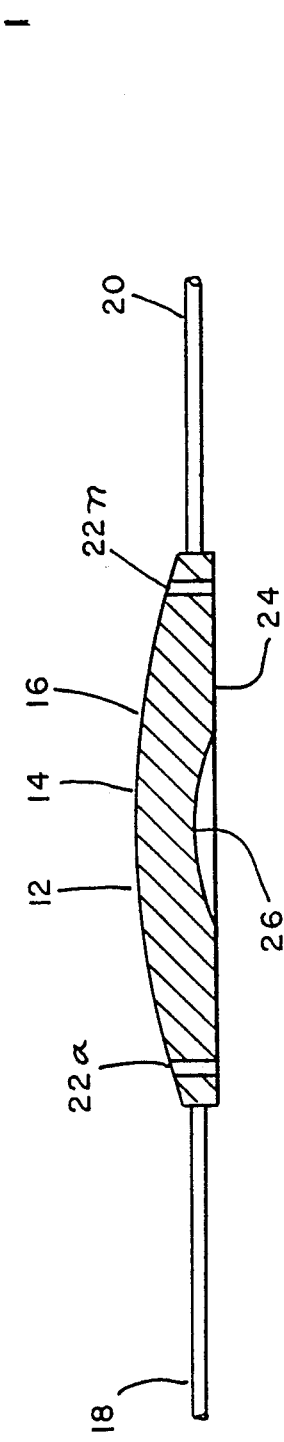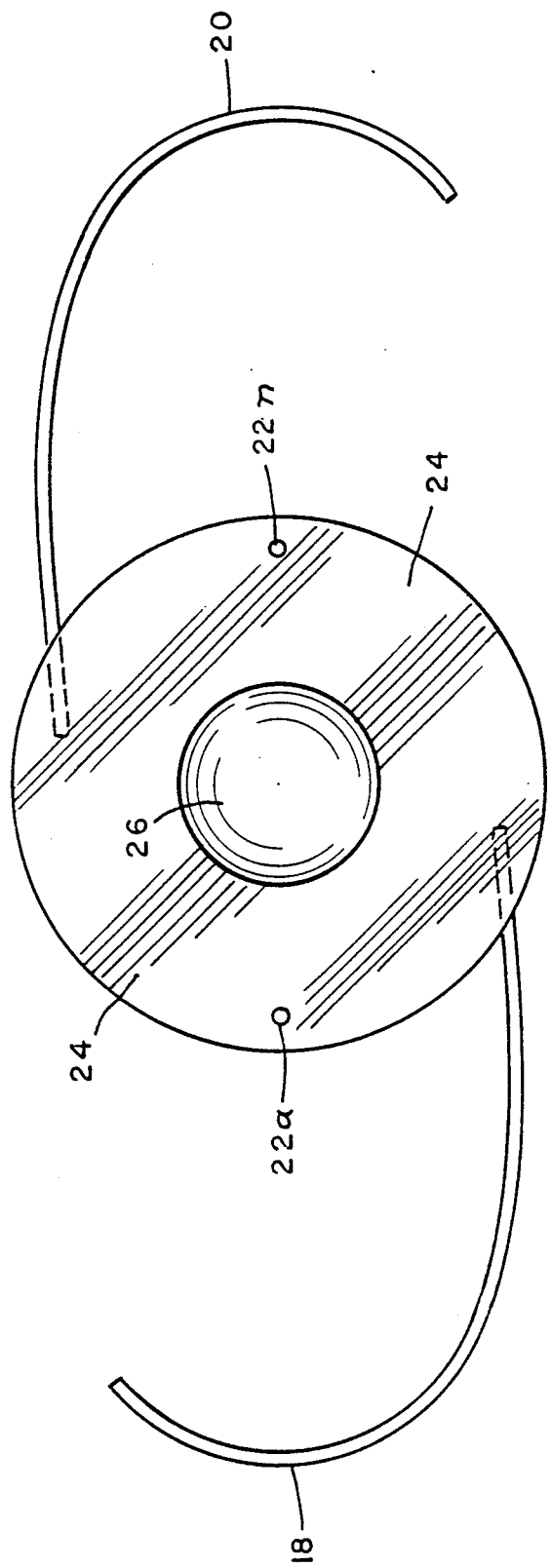

INTRAOCULAR LENS

CROSS REFERENCES TO CO-PENDING APPLICATIONS

This application is a continuation of U.S. Ser. No. 07/043,319, filed Apr. 28, 1987, entitled "Intraocular Lens", now abandoned, which is a continuation of U.S. Ser. No. 06/837,135, filed Mar. 7, 1986, entitled "Intraocular Lens", now abandoned.

BACKGROUND OF THE INVENTION

1. Field of the Invention

The present invention pertains to an intraocular lens, and more particularly, pertains to a dimpled YAG lens or YAG dimpled lens which includes a barrier rim, as well as YAG spacing geometrical section.

2. Background of the Invention

Prior art lenses with YAG spaces have not provided sufficient barriers which reduce the rate of capsular opacification from Elschnig's pearls. Two representative prior art intraocular lens patents are the Hoffer reissue patent No. 31,626 and the Myers reissue patent No. 31,998, which are designated in the art as YAG lenses Evidence is also accumulating that insertion of a posterior chamber lens implant may reduce the rate at which the posterior capsule opacifies, particularly if the convex surface of the optic is posterior in broad opposition to the capsule. This is commonly referred to as the "barrier effect". No one to date has performed a careful prospective study to be certain that posterior chamber lenses are a barrier to Elschnig's pearl-type capsular opacification, but many experienced surgeons agree that there is a beneficial effect.

In my experience, approximately 1 percent of capsules opacify in the first year following extracapsular cataract extraction and posterior chamber lens implantation. The majority of these cases are from a fibrous metaplasia and not from Elschnig's pearls. After this first year, approximately 5 percent of capsules opacify each year up to my current follow-up of approximately five years leading to an incidence of approximately 20–25 percent after five years follow-up.

This is a lower incidence than was experienced utilizing extracapsular cataract extraction without posterior chamber lens implantation or with anterior chamber or iridocapsular lens implantation. This reduction in the rate of capsular opacification when utilizing a posterior chamber lens has also been documented by Pearce, Gills, Anis, Harris, McIntrye and others. One can often clinically observe this retardation in the progression of Elschnig's pearls as they approach a posterior chamber lens that has adhered to the posterior capsule. On the other hand., it is not yet known if this delay in posterior capsular opacification is permanent. With the passage of enough time an increasing percentage of capsules may be expected to opacify. Nonetheless, this reduced rate of opacification is a significant advantage.

The firm and broad contact of the lens implant optic to the posterior capsule mentioned earlier may also provide the advantage of reducing the incidence of capsular opacification from Elschnig's pearls. It has been the clinical impression of several surgeons that a relative barrier to cortical cell proliferation and late posterior capsular opacification can be obtained when the lens implant optic adheres to the posterior capsule. This barrier effect appears to delay the onset of capsular opacification. If a primary discission is performed, the lens optic will, in some cases, tamponade the vitreous in the posterior chamber and the capsule can re-adhere to the posterior convex surface of the lens implant thereby recreating a barrier between the anterior and posterior chamber. If a secondary discission is required, the optic-capsular adhesion can be readily separated with a discission needle.

The present invention overcomes the disadvantages of the prior art by providing a YAG dimpled or dimpled YAG intraocular lens with an effective barrier rim.

SUMMARY OF THE INVENTION

The general purpose of the present invention is to provide a dimpled YAG intraocular lens which includes an effective barrier rim as a broad seal.

According to one embodiment of the present invention, there is provided a dimpled YAG lens with a barrier having a diametrical length of 2–4mm and a YAG space of a diametrical length of 3–4mm when the surface length optic diameter is about 6–7mm. The surface area of the barrier rim with respect to the surface area of the YAG space, is about 75–25 percent or in the range of 80 to 33 percent for the barrier rim with respect to the YAG space surface area. The lens optic can assume either a plano-convex or a bi-convex configuration and the YAG dimple can either be a concave surface or a substantially rectangular space. The dimple can also include a geometrical configuration, such as a Maltese cross, circular groove or trough, combination of a Maltese cross and circular groove, or other predetermined like geometrical configurations.

One significant aspect and feature of the present invention is an intraocular lens with a dimpled YAG space which utilizes a barrier rim which is effective in preventing migration of the pearls towards the visual access. The broad seal formed by the barrier rim remains intact and provides a suitable breadth of adhesion. This is based in that the barrier rim is approximately in the range of 80–33% or preferably 75 percent of the total area of the posterior surface of the lens by way of example and for purposes of illustration only, but not to be construed as limiting of the present invention.

Another significant aspect and feature of the present invention is an intraocular lens which provides a YAG laser opening which is approximately 3–4mm in diameter which is sufficient while the barrier rim is 3–4mm in longitudinal surface length measured on diametrical length.

Having thus described embodiments of the present invention, it is a principal object hereof to provide a dimpled YAG intraocular lens with an effective barrier rim.

One of the objects of the present invention is to provide a barrier rim which provides a broad seal, remains intact and maintains a breadth of adhesion. The barrier rim surface area is approximately in the range of 80–33%, preferably 75 percent of the total surface area of the intraocular lens. The other 25 percent of the surface area is for the YAG laser opening of the lens.

BRIEF DESCRIPTION OF THE DRAWINGS

FIG. 2 illustrates a cross-sectional view taken along line 2—2 of FIG. 1;

FIG. 3 illustrates a bottom view of FIG. 1;

DESCRIPTION OF THE PREFERRED EMBODIMENTS

Figure 1:
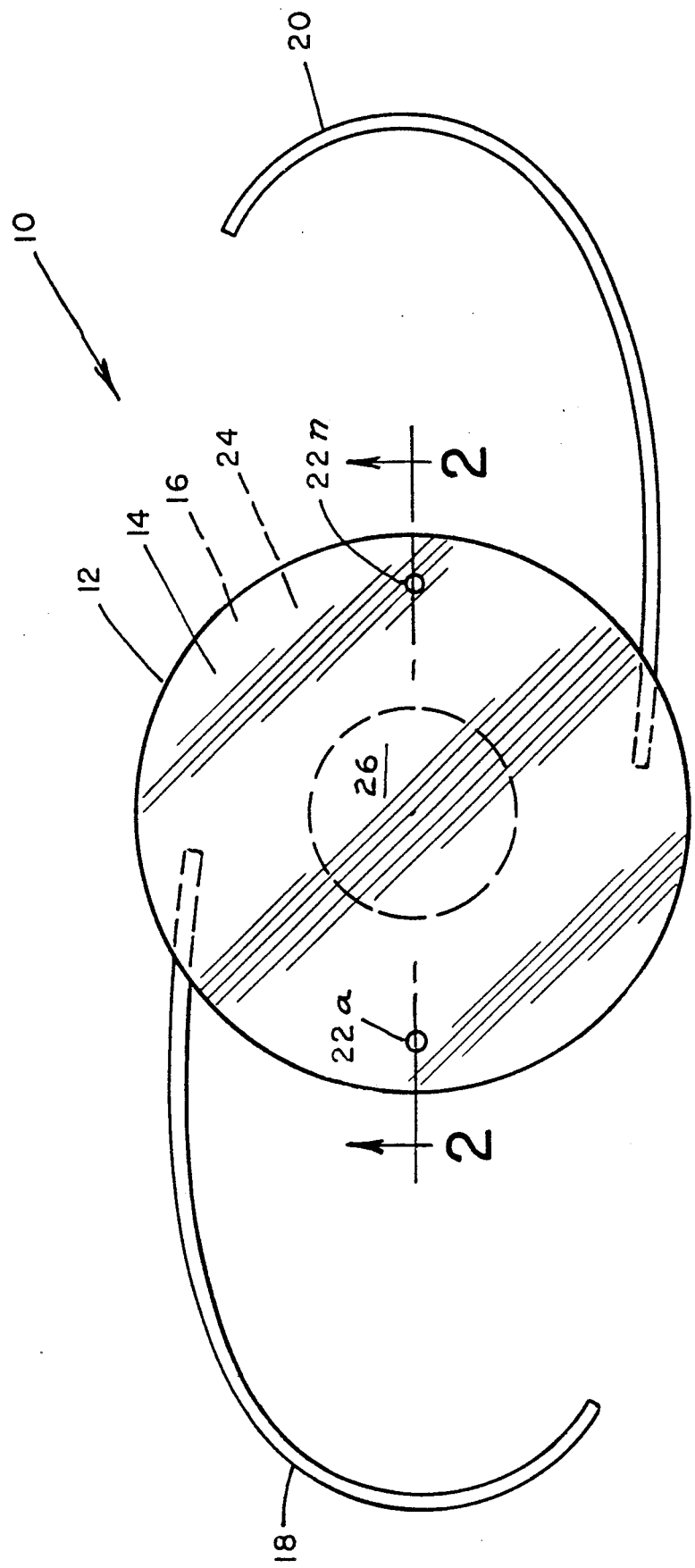
FIG. 1 illustrates a top view of a intraocular lens, a dimpled YAG lens, the present invention.

FIG. 1 illustrates a top view of an intraocular lens 10 including a lens optic 12, a convex surface 14, a planar surface 16, as illustrated in FIG. 2. Two loops 18 and 20 are secured to the lens optic accordingly as is understood in the art. A plurality of positioning holes 22a-22n can be provided accordingly about the circumference of the lens. The lens includes an effective barrier rim 24 and a YAG space 26, as now described in detail in FIG. 2. The barrier rim 24 extends inwardly from an edge of the optic 12.

FIG. 2 illustrates a cross-sectional side view taken along line 2—2 of FIG. 1 where all numerals correspond to those elements previously described. Particularly, the barrier rim 24 is illustrated as a plano surface for purposes of illustration and by way of example in this figure, and is not to be construed as limiting of the present invention. The YAG space opening 26 is concave by way of example and for purposes of illustration only, and is not be construed as limiting of the present invention. The surface area of the barrier rim 24 is approximately 80-33%, preferably 75 percent of the total surface area of the posterior side 16 of the lens.

FIG. 3 illustrates a bottom view of the lens 10 where all numerals correspond to those elements previously described.

Figure 4:
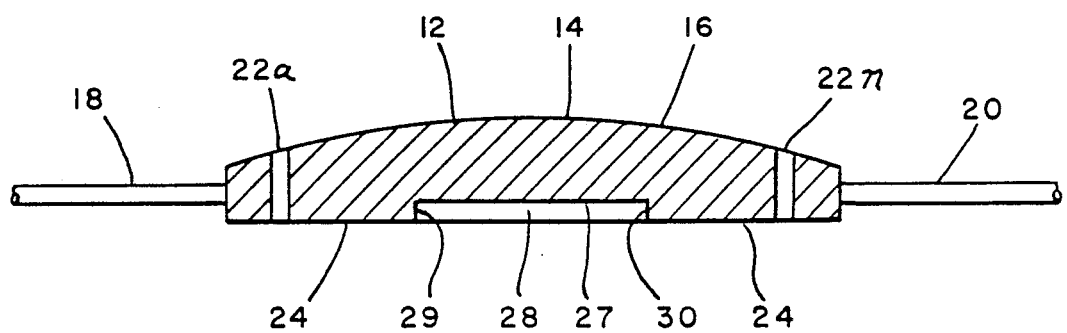
FIG. 4 illustrates a cross-sectional side view of an alternative embodiment.

FIG. 4 illustrates cross-sectional view of an alternative embodiment of FIG. 2 where the YAG opening 28, opposed to being concave, is cylindrical, having a planar upper surface 27 with its cross-section appearing rectangular like. The corners 29 and 30 can be radiused accordingly.

Figure 5:
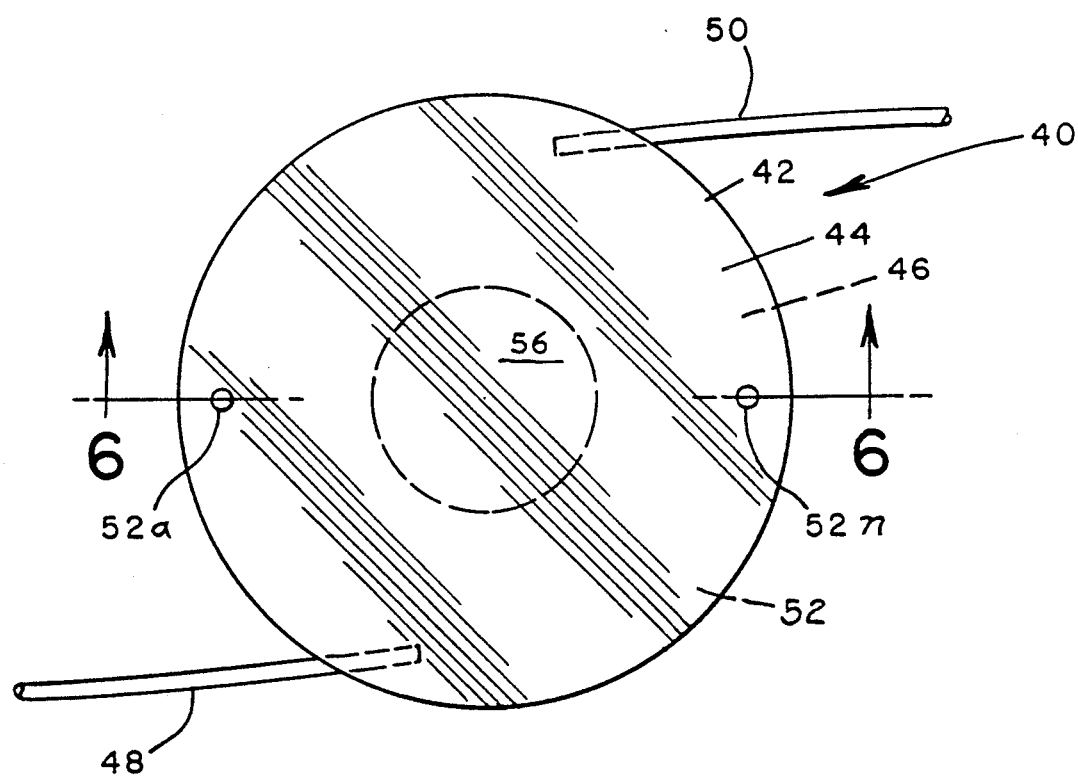
FIG. 5 illustrates a top view of another embodiment of a dimpled YAG lens.

FIG. 5 illustrates another embodiment of the present invention, a dimpled YAG intraocular lens 40 including a lens optic 42 having a bi-convex optic with convex surfaces 44 and 46 joined at an edge 45. Loops 48 and 50 likewise secure to the lens optic as previously discussed. Positioning holes 52a-52n are provided at predetermined locations about the circumference of the optic. The posterior side of the optic includes a barrier rim 54 and a YAG space 56 as now described in detail in FIG. 6.

Figure 6:
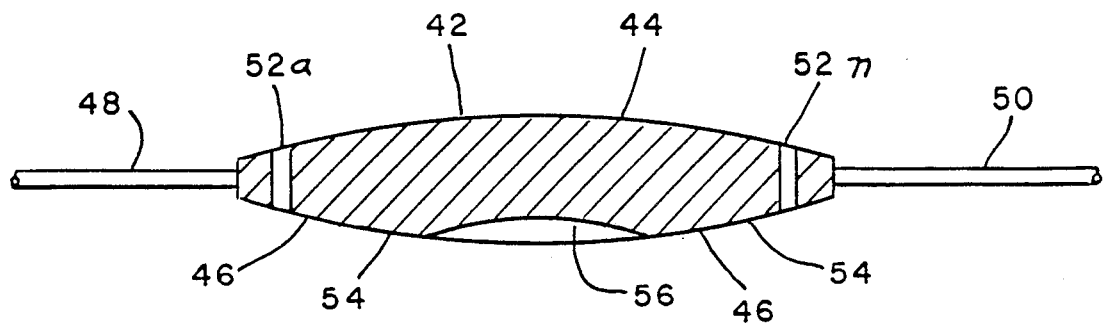
FIG. 6 illustrates a cross-sectional view taken along line 6—6 of FIG. 5.

FIG. 6 illustrates a cross-sectional view taken along line 6—6 of FIG. 5 and illustrates the barrier rim 54 and the YAG space 56. All numerals correspond to those elements previously described. The surface area of the barrier rim is about 80-33%, preferably 75 percent of the total surface area of the posterior surface area of the lens. The barrier rim can have a surface area in the range of 33 to 80 percent of the total posterior surface area of the lens as so predetermined.

Figure 7:
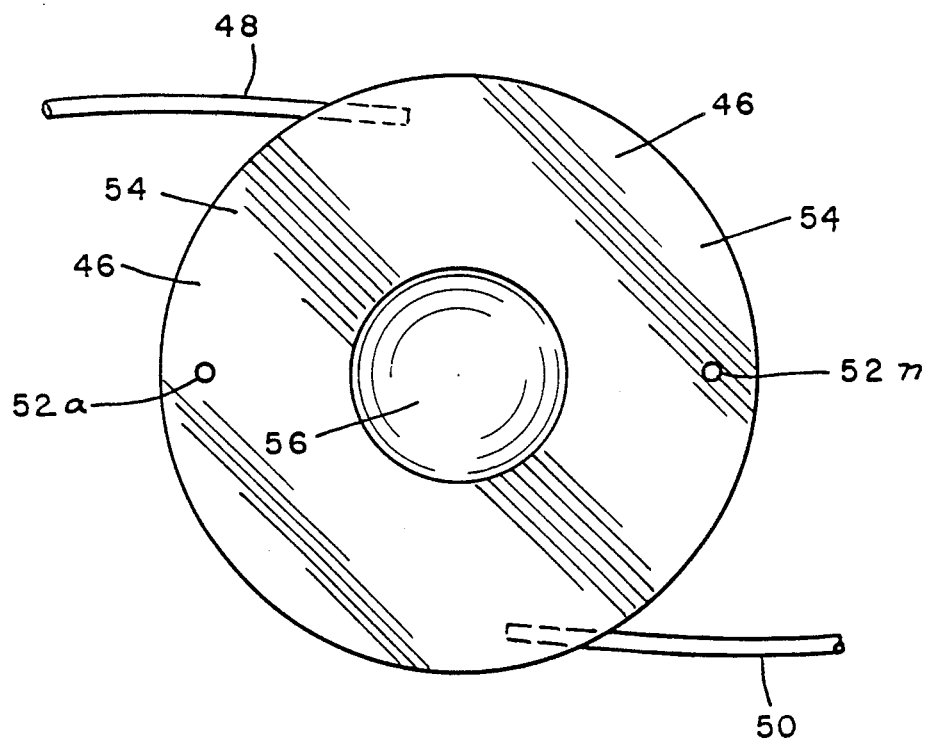
FIG. 7 illustrates a bottom view of FIG. 5.

FIG. 7 illustrates a bottom view of FIG. 5 where all numerals correspond to those elements previously described.

Figure 8:
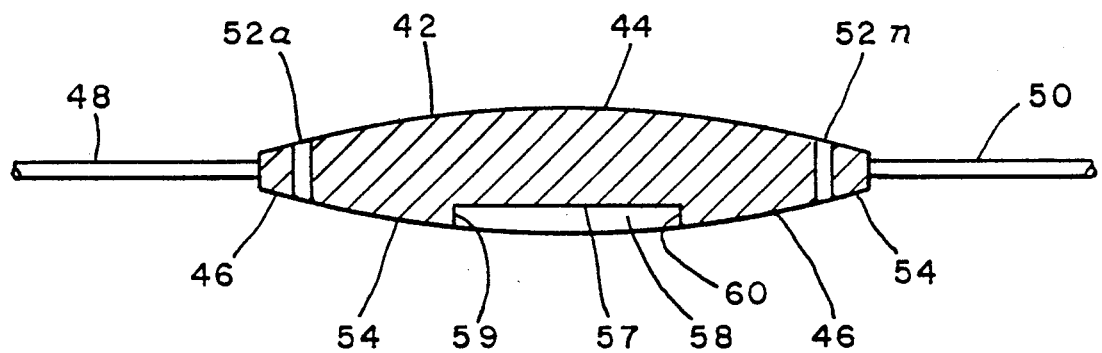
FIG. 8 illustrates an alternative embodiment of FIG. 6.

FIG. 8 illustrates an alternative embodiment of FIG. 6, illustrating a cylindrical cross section YAG section of FIG. 6. The YAG space 58 is cylindrical having a planar upper surface 57 with its cross section appearing rectangular. The corners 59 and 60 can be radiused accordingly.

FIGS. 9-14 illustrate views of alternative embodiments of the geometrical configurations for the YAG space. The lens optic can be either plano convex or bi-convex.

Figure 9:
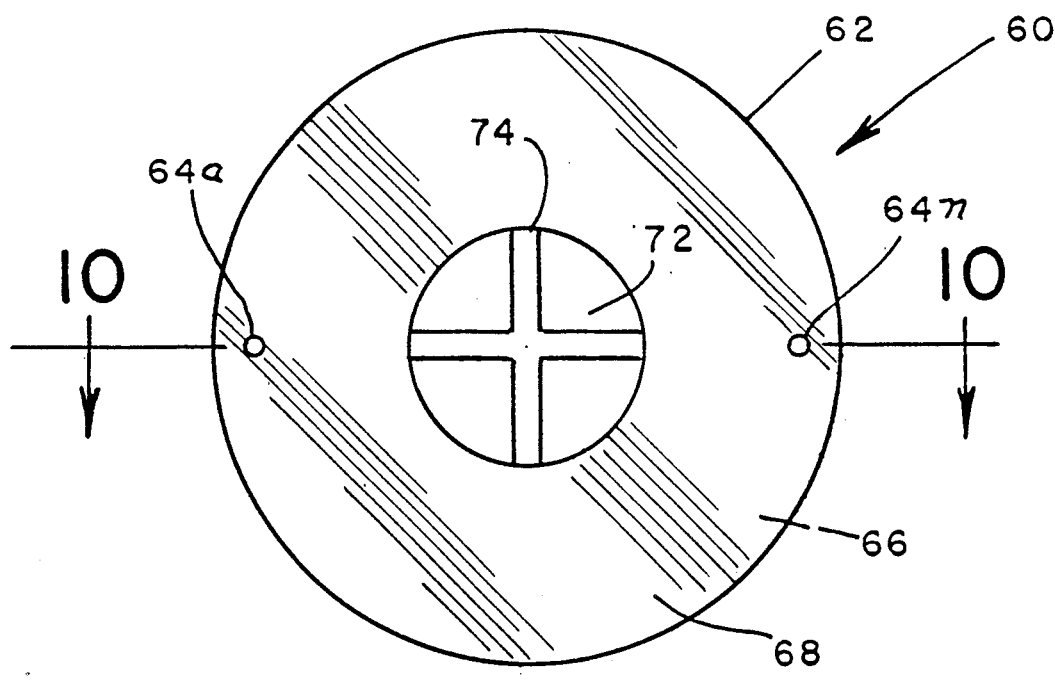
FIG. 9 illustrates a bottom view of a YAG opening having a Maltese cross geometry.

FIG. 9 illustrates a bottom view of a Maltese cross configuration of an intraocular lens 60 including a lens optic 62, positioning holes 64a-64n, a convex surface 66, an edge 67, a planar surface 68, a barrier rim 70, a concave YAG space 72, and a geometrically configured Maltese cross groove 74 centered within the concave YAG space 72. The lens optic can either be plano-convex or bi-convex. Loops are not illustrated as being attached to the lens for the sake of brevity and clarity in the illustration. The effective barrier rim. 70 has a surface area of about 75% of the total surface area of the posterior surface of the lens or in a range of 33-80%.

Figure 10:
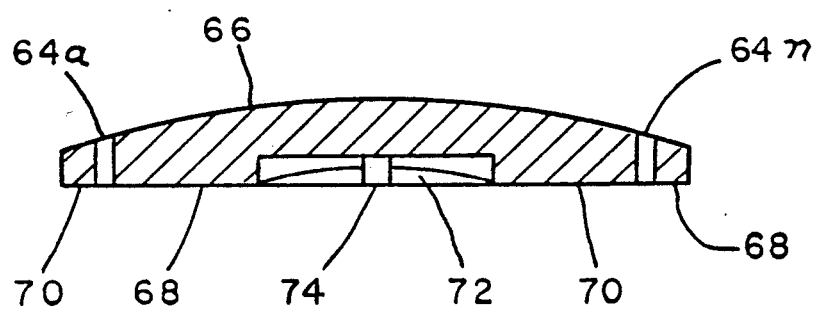
FIG. 10 illustrates a cross-sectional side view taken along line 10—10 of FIG. 9.

FIG. 10 illustrates a cross-sectional side view taken along line 10—10 of FIG. 9 where all numerals correspond to those elements previously described.

Figure 11:
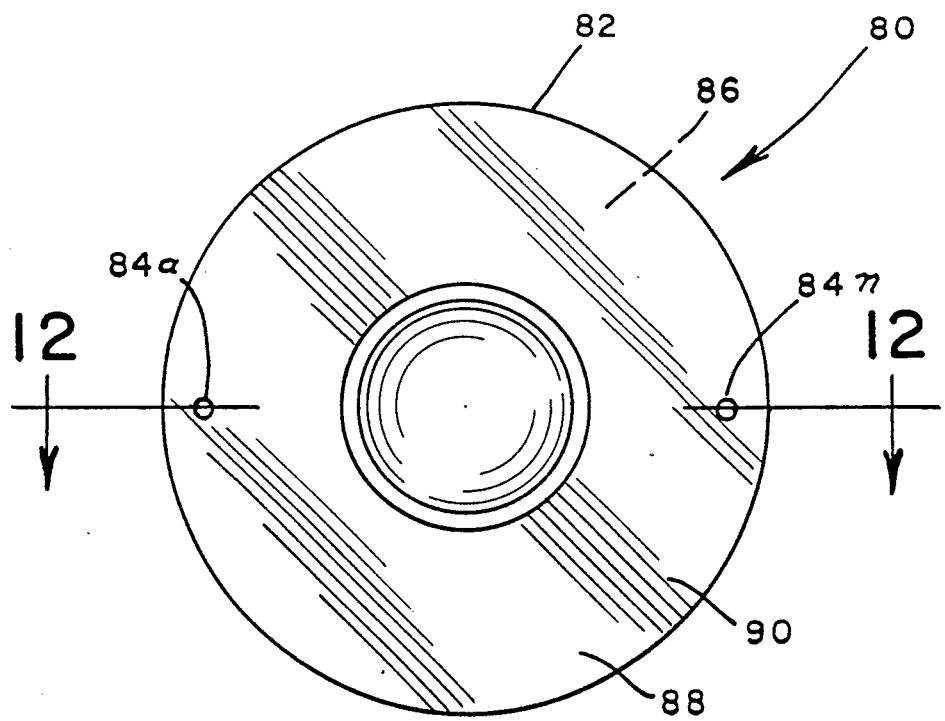
FIG. 11 illustrates a bottom view of a YAG opening of a circular groove.

FIG. 11 illustrates a bottom view of a dimpled YAG intraocular lens 80 with a YAG space concentric within a circular groove, including a lens optic 82, positioning holes 84a—84n, a convex surface 86, an edge 87, a planar surface 88, a barrier rim 90 and a concave YAG space 92 concentric within annular groove 94. The lens optic can be either plano-convex or bi-convex. Loops are not illustrated as being attached to the lens for sake of brevity and clarity in the illustration. The barrier rim 90 is again in a range of 33% to 80% of the surface area of the posterior surface of the lens.

Figure 12:
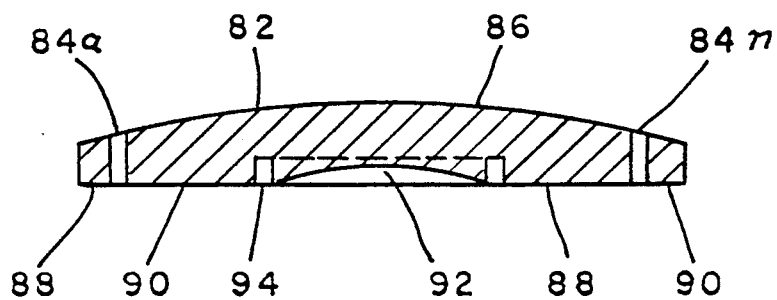
FIG. 12 illustrates a cross-sectional side view along line 12—12 of FIG. 11.

FIG. 12 illustrates a cross-sectional side view taken along line 12—12 of FIG. 11 where all numerals correspond to those elements previously described.

Figure 13:
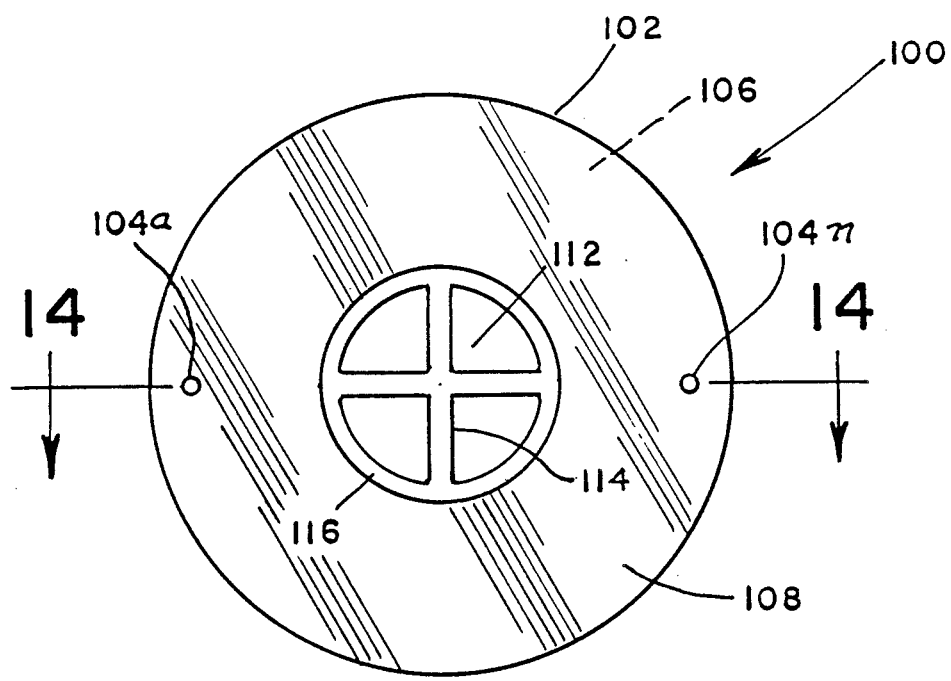
FIG. 13 illustrates a bottom view of a YAG opening of a circular groove with a Maltese cross configuration; and, FIG. 14 illustrates a cross-sectional side view taken along line 14—14 of FIG. 13.

FIG. 13 illustrates a bottom view of an intraocular lens 100 where the YAG space is a Maltese cross contained within a circular groove configuration, including a lens optic 102, positioning holes 104a-104n, a convex surface 106, a planar surface 108, a barrier rim 110, a concave YAG space 112 and a geometrically configured Maltese cross groove 114 centered within annular groove 116. The lens can be either, plano-convex or bi-convex. Loops are not illustrated as being attached to the lens for sake of brevity and clarity in the illustration. Again, the barrier rim can have a surface area of 33% to 80% of the total surface area of the posterior surface of the lens.

Figure 14:
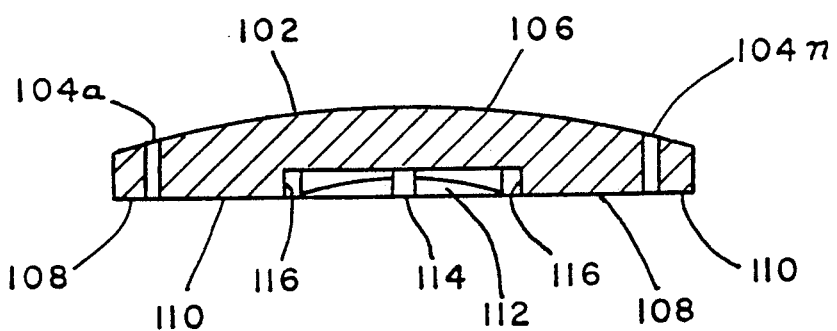

FIG. 14 illustrates a cross-sectional side view taken along line 14—14 of FIG. 13 where all numerals correspond to those elements previously described.

Various modifications can be made to the lens of the present invention without departing from the apparent scope thereof.

I claim:
1. Intraocular lens comprising:
   a. lens optic;
   b. YAG space on the posterior surface of said lens optic, said YAG spacing having the shape of a Maltese cross; and,
   c. barrier rim between an edge of said lens optic and said YAG space, said barrier rim having a surface area of 33%-80% of the total surface area of the posterior surface of said lens optic whereby said barrier rim is effective.

2. Intraocular lens comprising:
   a. lens optic;
   b. YAG space on the posterior surface of said lens optic, said YAG space having the shape of a Maltese cross in a circular groove; and,
   c. barrier rim between an edge of said lens optic and said YAG space, said barrier rim having a surface area of 33%-80% of the total surface area of the posterior surface of said lens optic whereby said barrier rim is effective.

* * * * *